United States Patent
Terai et al.

(10) Patent No.: US 11,954,850 B2
(45) Date of Patent: Apr. 9, 2024

(54) MEDICAL INFORMATION PROCESSING SYSTEM AND MEDICAL INFORMATION PROCESSING METHOD

(71) Applicant: CANON MEDICAL SYSTEMS CORPORATION, Otawara (JP)

(72) Inventors: Koichi Terai, Shioya-gun (JP); Hiroki Saito, Otawara (JP); Kenichi Usui, Nasushiobara (JP); Yosuke Okubo, Nasushiobara (JP); Hirobumi Nonaka, Yaita (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 284 days.

(21) Appl. No.: 17/173,248

(22) Filed: Feb. 11, 2021

(65) Prior Publication Data
US 2021/0272278 A1 Sep. 2, 2021

(30) Foreign Application Priority Data

Feb. 28, 2020 (JP) .................................. 2020-033940
Jan. 13, 2021 (JP) .................................. 2021-003734

(51) Int. Cl.
*G06T 7/00* (2017.01)
*A61B 5/055* (2006.01)
(Continued)

(52) U.S. Cl.
CPC ........... *G06T 7/0012* (2013.01); *G16H 10/60* (2018.01); *G16H 30/20* (2018.01); *G16H 30/40* (2018.01);
(Continued)

(58) Field of Classification Search
CPC ..... G06T 7/0012; G06T 2200/24; G06T 7/10; G06T 2207/30096; G06T 2207/30101;
(Continued)

(56) References Cited

U.S. PATENT DOCUMENTS 7,162,061 B1 * 1/2007 Takeo ................... G06T 7/0012
382/128
10,140,421 B1 * 11/2018 Bernard ................. A61B 6/563
(Continued)

FOREIGN PATENT DOCUMENTS

JP  2004357866 A  * 12/2004
JP  2006-511882 A     4/2006
(Continued)

OTHER PUBLICATIONS

Machine translation of WO-2019107134-A1 (Year: 2019).*
Machine translation of JP-2004357866-A (Year: 2004).*

*Primary Examiner* — John Villecco
*Assistant Examiner* — Courtney Joan Nelson
(74) *Attorney, Agent, or Firm* — Oblon, McClelland, Maier & Neustadt, L.L.P.

(57) ABSTRACT

A medical information processing system according to an embodiment includes processing circuitry and a display. On the basis of one of the type of at least one abnormality detection algorithm to which a medical image related to an examined subject is to be input and information relevant to an abnormality detected by inputting the medical image to the abnormality detection algorithm, the processing circuitry judges whether or not urgency is present in a disorder related to the abnormality. When it is determined that the urgency is present, the display displays, in an examination list of examination orders, assessment information related to assessing the abnormality and urgency information indicating the urgency so as to be positioned adjacent to any of the examination orders related to the abnormality.

7 Claims, 9 Drawing Sheets

(51) Int. Cl.
    *A61B 6/00*          (2006.01)
    *G06F 3/04812*     (2022.01)
    *G06F 3/0482*      (2013.01)
    *G06F 3/04845*     (2022.01)
    *G16H 10/60*      (2018.01)
    *G16H 30/20*      (2018.01)
    *G16H 30/40*      (2018.01)
    *G16H 50/20*      (2018.01)
    *G16H 50/30*      (2018.01)
    *A61B 6/50*       (2024.01)

(52) U.S. Cl.
    CPC ............. *G16H 50/20* (2018.01); *G16H 50/30* (2018.01); *A61B 5/055* (2013.01); *A61B 6/504* (2013.01); *G06F 3/04812* (2013.01); *G06F 3/0482* (2013.01); *G06F 3/04845* (2013.01); *G06T 2207/30101* (2013.01)

(58) Field of Classification Search
    CPC ........ G16H 10/00; G16H 15/00; G16H 50/20; G16H 30/20; G16H 40/20; G16H 50/30; G16H 10/60; G16H 30/40; G06F 3/048; G06F 18/24; G06F 18/231; G06F 18/2431; G06F 18/00; G06F 3/04812; G06F 3/0482; G06F 3/04845; A61B 6/5217; A61B 8/5223; A61B 5/7264; A61B 6/5211; A61B 5/055; A61B 6/504; G06V 2201/03; G06V 10/25; G06V 30/19173; G06V 10/776
    See application file for complete search history.

(56) References Cited

U.S. PATENT DOCUMENTS

| | | | | |
|---|---|---|---|---|
| 2004/0083257 | A1* | 4/2004 | Gortler | G16H 10/60 709/201 |
| 2004/0122787 | A1 | 6/2004 | Avinash et al. | |
| 2005/0041844 | A1* | 2/2005 | Yamanaka | G06T 7/0012 382/128 |
| 2007/0185730 | A1* | 8/2007 | Mahesh | G06Q 10/0633 705/2 |
| 2008/0152086 | A1* | 6/2008 | Hall | A61B 6/5235 378/98.2 |
| 2020/0075144 | A1* | 3/2020 | Nakatsugawa | G16H 10/40 |

FOREIGN PATENT DOCUMENTS

| | | | | |
|---|---|---|---|---|
| WO | WO-2013036842 A2 * | 3/2013 | | G06F 16/50 |
| WO | WO-2017011532 A1 * | 1/2017 | | |
| WO | WO-2017218773 A1 * | 12/2017 | | G06K 9/00469 |
| WO | WO-2019107134 A1 * | 6/2019 | | A61B 5/0042 |

* cited by examiner

FIG.3

ALT

| DISORDER NAME | EXAMINATION PURPOSE | ABNORMALITY DETECTED | PRESENCE OF URGENCY |
|---|---|---|---|
| ICH | FOLLOW-UP | YES | NO |
| | | NO | |
| | URGENT EXAMINATION | YES | YES |
| | | NO | NO |
| LVO | FOLLOW-UP | YES | NO |
| | | NO | |
| | URGENT EXAMINATION | YES | YES |
| | | NO | NO |
| ⋮ | ⋮ | ⋮ | ⋮ |

MEDICAL INFORMATION PROCESSING SYSTEM AND MEDICAL INFORMATION PROCESSING METHOD

CROSS-REFERENCE TO RELATED APPLICATIONS

This application is based upon and claims the benefit of priority from Japanese Patent Application No. 2020-033940, filed on Feb. 28, 2020; and Japanese Patent Application No. 2021-003734, filed on Jan. 13, 2021, the entire contents of both of which are incorporated herein by reference.

FIELD

Embodiments described herein relate generally to a medical information processing system and a medical information processing method.

BACKGROUND

Conventionally, a worklist is known which displays a sequential order of performing medical examinations (hereinafter, "examinations") with which an image diagnosing process is to be performed by a radiologist. By using the displayed worklist, the radiologist inputs an instruction related to displaying any of the examinations. In this situation, a medical image related to the examination indicated in the instruction is displayed on a viewer. The radiologist interprets the displayed medical image and writes a diagnosis result in an image interpretation report which may be called an image diagnosis report. For example, when an urgent image interpretation is necessary for an acute medical case or the like, a marker indicating the urgency is displayed in the worklist. In that situation, the radiologist interprets images while prioritizing the examination having the urgency marker appended thereto.

In recent years, due to the advancement of image processing techniques for medical images, it is becoming possible to detect abnormalities from medical images by using a computer algorithm related to a Computer-Aided Diagnosis (hereinafter, "CAD") scheme, for example. Examples of the abnormalities that can be detected by using such a computer algorithm include acute disorders such as acute appendicitis, acute myocardial infarction, and cerebral infarction. Acute disorders denote abnormalities that require an urgent diagnosis and/or treatment. However, the precision level of the abnormality detection using such a computer algorithm is not perfect. In other words, acute disorders detected by using computer algorithms cannot all be correct. For this reason, some radiologists may prioritize interpreting medical images related to acute disorders detected by computer algorithms. On such occasion, a situation may arise where the detection turns out to be an erroneous detection by a computer algorithm and, in fact, there was no need for the radiologist to interpret the image urgently.

BRIEF DESCRIPTION OF THE DRAWINGS

FIG. 3 is a drawing illustrating an example of a purpose-added correspondence table according to the embodiment;

DETAILED DESCRIPTION

Figure 1:
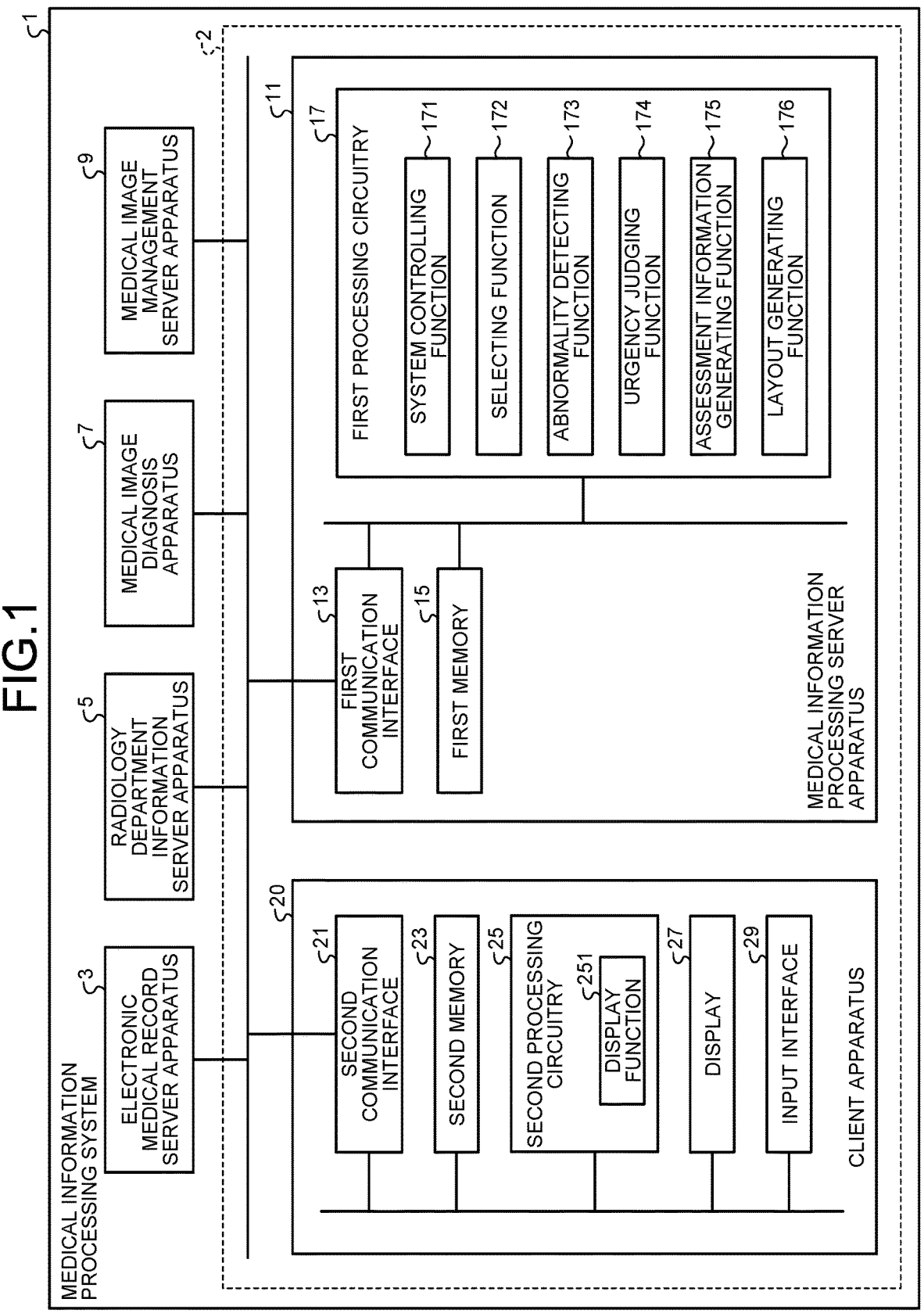
FIG. 1 is a diagram illustrating an exemplary configuration of a medical information processing system according to an embodiment.

Exemplary embodiments of a medical information processing system, a medical information processing method, and a medical information processing program will be explained in detail below, with reference to the accompanying drawings. In the description of the embodiments below, some of the constituent elements that are referred to by using the same reference characters are assumed to perform the same operations, and duplicate explanations thereof may be omitted as appropriate. Further, possible embodiments of the medical information processing system of the present disclosure are not limited to the embodiments described below.

Embodiments

A medical information processing system according to an embodiment includes processing circuitry and a display. On the basis of one of the type of at least one abnormality detection algorithm to which a medical image related to an examined subject is to be input and information relevant to an abnormality detected by inputting the medical image to the abnormality detection algorithm, the processing circuitry is configured to judge whether or not urgency is present in a disorder related to the abnormality. When it is determined that the urgency is present, the display is configured to display, in an examination list presenting a list of examination orders, assessment information related to assessing the abnormality and urgency information indicating the urgency so as to be positioned adjacent to any of the examination orders related to the abnormality.

An overall configuration of a medical information processing system according to an embodiment will be explained. FIG. 1 is a diagram illustrating an exemplary configuration of a medical information processing system 1 according to the embodiment. The medical information processing system 1 includes: an electronic medical record server apparatus 3, a radiology department information server apparatus 5, a medical image diagnosis apparatus 7, a medical image management server apparatus 9, a medical information processing server apparatus 11, and a client apparatus 20. In the medical information processing system 1, one or more client apparatuses 20 may be provided for each of the abovementioned various types of server apparatuses, to serve as one or more terminal devices. Although the medical information processing system 1 is described as a client server system as illustrated in FIG. 1, possible embodiments thereof are not limited to this example. For instance, as indicated with a dotted-line box 2 in FIG. 1, the medical information processing system 1 may be configured so as to include the medical information processing server apparatus 11 and the client apparatus 20. Further, the various types of server apparatuses in the medical information processing system 1 may be realized as an integration server in which functions of the server apparatuses are integrated together. In other words, the server apparatuses in the medical information processing system 1 may be realized as the single integration server.

Alternatively, the medical information processing system 1 may be realized as a stand-alone medical information processing apparatus. In that situation, the medical information processing apparatus includes: a communication interface in which functions and the like of a first communication interface 13 and a second communication interface 21 are integrated together as necessary; a memory (a storage unit) in which stored contents and the like of a first memory 15 and a second memory 23 are integrated together as necessary; processing circuitry (one or more processing units) in which functions and the like of first processing circuitry 17 and second processing circuitry 25 are integrated together as necessary; a display 27 (a display unit); and an input interface 29 (an input unit).

The electronic medical record server apparatus 3 and a terminal device (hereinafter, "electronic medical record terminal device") electrically connected to the electronic medical record server apparatus 3 structure an electronic medical record system. The electronic medical record system is an information system configured to manage electronic medical records for recording details of diagnoses and treatments. The electronic medical record server apparatus 3 is a computer apparatus configured to perform processes related to managing the electronic medical records. The electronic medical record terminal device is used by medical doctors, nurses, and the like who input and reference the electronic medical records. The electronic medical record server apparatus 3 and the electronic medical record terminal device are connected to a communication network. In response to an instruction from a clinician, the electronic medical record terminal device is configured to input an examination order for an examined subject (hereinafter, "patient"). When the examination order instructs imaging the patient related to an image diagnosing process, the examination order includes, for example, an examined site, an examination type (information related to details of the examination such as a modality), the name of a disorder (hereinafter, "disorder name"), and a purpose of the examination (hereinafter, "examination purpose"). Further, the examination order may also include information such as a patient ID of the patient undergoing the examination, the patient's name, an examination ID, and the date of the examination. In response to the input of the examination order, the electronic medical record server apparatus 3 is configured to transmit the examination order to the radiology department information server apparatus 5, together with patient information of the patient or the like.

The radiology department information server apparatus 5 and a terminal device (hereinafter, "radiology department terminal device") electrically connected to the radiology department information server apparatus 5 structure a radiology department information system (hereinafter, "Radiology Information System [RIS]"). The RIS is an information system configured to manage information in the radiology department of a hospital. The radiology department information server apparatus (hereinafter, "RIS server") 5 is a computer apparatus configured to perform processes related to managing the information in the radiology department. As an example of operations, the RIS server 5 is configured to receive the examination order from the electronic medical record server apparatus 3 and to obtain, from within the examination order, information (e.g., the examination type) related to the medical image diagnosis apparatus 7. The RIS server 5 is configured to transmit the examination order to the medical image diagnosis apparatus 7 specified in the examination order. In an example, when the examination order is transmitted to the medical image diagnosis apparatus 7, the RIS server 5 may add information such as the patient ID and the date of examination to a Digital Imaging and Communications in Medicine (DICOM) tag or the like. The radiology department terminal device may be used by radiologists for creating image interpretation reports related to medical images.

The medical image diagnosis apparatus 7 is, for example, an apparatus configured to acquire medical images, such as an X-ray diagnosis apparatus, an X-ray Computed Tomography (CT) apparatus, or a Magnetic Resonance Imaging (MRI) apparatus. On the basis of the examination order received from the RIS server 5, the medical image diagnosis apparatus 7 is configured to perform an imaging process on the patient, in response to an operation performed by a technologist or the like to start the imaging process. As a result of the imaging process being executed, the medical image diagnosis apparatus 7 is configured to acquire data representing a state of a tissue inside the body of the patient. The medical image diagnosis apparatus 7 is configured to generate a medical image on the basis of the data and to transmit the generated medical image to the medical image management server apparatus 9, together with the examination order. Further, the medical image diagnosis apparatus 7 is configured to transmit the generated medical image to the medical information processing server apparatus 11.

The medical image management server apparatus 9 and a terminal device (hereinafter, "image management terminal device") electrically connected to the medical image management server apparatus 9 structure a medical image management system (hereinafter, "Picture Archiving and Communication System [PACS]"). The PACS is an information system configured to manage medical images such as X-ray CT images and Magnetic Resonance (MR) images, as well as image interpretation reports which may be called image diagnosis reports. The medical image management server apparatus (hereinafter, "PACS server") 9 is a computer apparatus configured to perform processes related to managing the medical images. Upon receipt of the medical image and the examination order from the medical image diagnosis apparatus 7, the PACS server 9 is configured to store therein the medical image and the examination order so as to be kept in association with each other. The medical image has appended thereto meta information (hereinafter, "appended information") of DICOM. The appended information includes the patient's name, a patient ID, a description related to the medical image (e.g., the slice thickness, a slice number, whether or not contrast enhancement was used), and the like. The image management terminal device may be used by radiologists for creating image interpretation reports, for example.

The medical information processing server apparatus 11 includes the first communication interface 13, the first memory 15, and the first processing circuitry 17. Alternatively, the first memory 15 and the first processing circuitry 17 may be incorporated in another server apparatus such as the PACS server 9.

For example, the first communication interface 13 is configured to perform data communication between the electronic medical record server apparatus 3, the RIS server 5, the PACS server 9, and the second communication interface 21. The communication standard used by the first communication interface 13 may be any standard. Examples thereof include Hearth Level 7 (HL7), DICOM, and a combination of the two. The first communication interface 13 is configured to output data obtained through the data communication with the various types of server apparatuses, to the first memory 15. Via the second communication interface 21, the first communication interface 13 is configured to receive an electrical signal of an input operation input to the input interface 29 of the client apparatus 20. The first communication interface 13 is configured to output the received electrical signal to the first processing circuitry 17.

The first memory 15 is a storage device storing therein various types of information, such as a Hard Disk Drive (HDD), a Solid State Driver (SSD), or an integrated circuit storage device. Other than an HDD or an SDD, the first memory 15 may be a portable storage medium such as a Compact Disc (CD), a Digital Versatile Disc (DVD), or a flash memory or may be a driving device configured to read and write various types of information from and to a semiconductor memory element such as a Random Access memory (RAM).

The first memory 15 has stored therein various types of programs related to the present embodiment. The first memory 15 stores therein data generated as a result of executing a selecting function 172, an abnormality detecting function 173, an urgency judging function 174, an assessment information generating function 175, and a layout generating function 176. The generated data and these functions will be explained later. Via the first communication interface 13, the first memory 15 is configured to store therein various types of diagnosis/treatment information acquired from the various types of server apparatuses and the medical image diagnosis apparatus 7. For example, the first memory 15 stores therein the examination order and at least one medical image taken according to the examination order. The examination order is obtained by the first processing circuitry 17, from either the electronic medical record server apparatus 3 or the RIS server 5, for example, via the first communication interface 13. The medical image is obtained by the first processing circuitry 17 from either the medical image diagnosis apparatus 7 or the PACS server 9, via the first communication interface 13.

The first memory 15 has stored therein one or more algorithms (hereinafter, "abnormality detection algorithms") each configured, by using a medical image, to detect at least one abnormality from the medical image. For example, the first memory 15 has stored therein a plurality of abnormality detection algorithms in accordance with types of abnormalities, types of medical images corresponding to types of the medical image diagnosis apparatus 7, imaged sites of the patient, and the like. For example, each of the abnormality detection algorithms corresponds to an analysis application program configured to receive an input of a medical image and to output, as an abnormality detection result, an abnormal section in the medical image, the disorder name related to the abnormality, various types of numerical values related to the abnormality, and accuracy of the disorder name, and the like. The abnormality detection result includes, for example, an overlay image and abnormality relevance information. The overlay image corresponds to an image in which the abnormal section expressed in a different hue than that of the medical image is superimposed on the medical image. The abnormality relevance information corresponds to information relevant to the abnormality such as the disorder name, the various types of numerical values related to the abnormality, and the accuracy of the disorder name.

The first memory 15 has stored therein one of: a correspondence table (hereinafter, "disorder urgency correspondence table") indicating whether or not urgency is present with regard to disorder names; and a correspondence table (hereinafter, "algorithm urgency correspondence table") indicating whether or not urgency is present with regard to types of the abnormality detection algorithms. Further, the first memory 15 may store therein a correspondence table (hereinafter, "purpose-added correspondence table") in which examination purposes are further added to the one of the disorder urgency correspondence table and the algorithm urgency correspondence table.

The analysis application program may be, for example, a trained model such as a Deep Neural Network (DNN), a rule-based analysis program, or the like. Possible examples of the abnormality detection algorithms are not limited to these and may be any of various types of computer algorithms related to Computer-Aided Diagnosis (hereinafter, "CAD") schemes. The first memory 15 has stored therein a percentage of disorder names that are output (hereinafter, "correct output percentage") by each abnormality detection algorithm being correct, so as to be kept in correspondence with the relevant abnormality detection algorithm. The correct output percentage may be determined, for example, in accordance with judgement results ("accept" and "ignore") input by radiologists in response to abnormality detection results displayed on the display 27. In other words, the correct output percentage varies depending on the judgment results input by the radiologists in response to the abnormality detection results.

Alternatively, the abnormality detection algorithms may be stored in a memory of an analysis server apparatus (hereinafter, "analysis server") configured to detect abnormalities from medical images. In this situation, the medical information processing system 1 further includes the analysis server. Further, the correct output percentage and the abnormality detection results may be stored in a memory of the PACS server 9. In that situation, the PACS server 9 is configured to tally judgment results input by radiologists in response to the abnormality detection results from the client apparatus 20 and to update the correct output percentage.

For example, the first processing circuitry 17 includes, as hardware resources, a processor such as a Central Processing Unit (CPU), a Micro Processing Unit (MPU), or a Graphics Processing Unit (GPU) and a memory such as a Read-Only Memory (ROM) or a RAM. Further, the first processing circuitry 17 may be realized by using an Application Specific Integrated Circuit (ASIC), a Field Programmable Gate Array (FPGA), or other devices such as a Complex Programmable Logic Device (CPLD) or a Simple Programmable Logic Device (SPLD).

The first processing circuitry 17 includes a system controlling function 171, a selecting function 172, an abnormality detecting function 173, an urgency judging function 174, an assessment information generating function 175, and a layout generating function 176. As for the system controlling function 171, the selecting function 172, the abnormality detecting function 173, the urgency judging function 174, the assessment information generating function 175, and the layout generating function 176, the functions thereof are stored in the first memory 15 in the form of computer-executable programs. By employing a processor configured to execute the programs loaded into a memory, the first processing circuitry 17 is configured to execute the system controlling function 171, the selecting function 172, the abnormality detecting function 173, the urgency judging function 174, the assessment information generating function 175, and the layout generating function 176.

In other words, the first processing circuitry 17 corresponds to a processor configured to realize the functions corresponding to the programs by reading and executing the programs from the first memory 15. That is to say, the first processing circuitry 17 that has read the programs has the functions corresponding to the read programs. In this situation, the functions (171 to 176) do not necessarily have to be realized by a single piece of processing circuitry. It is also acceptable to structure processing circuitry by combining together a plurality of independent processors, so that the functions (171 to 176) are realized as a result of the processors executing the programs.

By employing the system controlling function 171, the first processing circuitry 17 is configured to control the functions of the first processing circuitry 17, on the basis of an electrical signal corresponding to an input operation received from the operator via the input interface 29. More specifically, the first processing circuitry 17 is configured to read a control program stored in the first memory 15, to load the read control program into a memory in the first processing circuitry 17, and to control functional units of the medical information processing server apparatus 11 according to the loaded control program. When any of the abnormality detection algorithms is installed in the analysis server, it means that the processing circuitry (the processor) of the analysis server includes the selecting function 172 and the abnormality detecting function 173. Further, the system controlling function 171, the urgency judging function 174, the assessment information generating function 175, and the layout generating function 176 may be installed in the PACS server 9. In other words, the various types of functions of the medical information processing server apparatus 11 may be provided in the analysis server and the PACS server 9 in a distributed manner, as appropriate. In that situation, the medical information processing server apparatus 11 is realized by the combination of the analysis server and the PACS server 9.

On the basis of the medical image related to the patient, the selecting function 172 is configured to select at least one abnormality detection algorithm to which the medical image is to be input. By inputting the medical image to the selected abnormality detection algorithm, the abnormality detecting function 173 is configured to detect an abnormality from the medical image. On the basis of one of information related to the abnormality and the type of the abnormality detection algorithm, the urgency judging function 174 is configured to judge whether or not urgency is present in a disorder related to the abnormality, i.e., whether or not a diagnosis/treatment is urgently needed by the disorder related to the detected abnormality. In an example, the urgency judging function 174 may judge whether or not the urgency is present, by further using the examination purpose in the examination order for the patient related to the medical image. On the basis of an output from the abnormality detection algorithm, the assessment information generating function 175 is configured to generate information (hereinafter, "assessment information") for assessing urgency of the abnormality detected by the abnormality detection algorithm. When it is determined the urgency is present, the layout generating function 176 is configured to generate a layout (hereinafter, "assessment layout") in which it is possible for a radiologist to assess the abnormality and which is related to displaying the medical image including the detecting abnormality. The assessment layout corresponds to a display layout suitable for an image interpretation environment for the medical image related to the detected abnormality.

The first processing circuitry 17 realizing the system controlling function 171, the selecting function 172, the abnormality detecting function 173, the urgency judging function 174, the assessment information generating function 175, and the layout generating function 176 is an example of a system controlling unit, a selecting unit, an abnormality detecting unit, an urgency judging unit, an assessment information generating unit, and a layout generating unit. The selecting function 172, the abnormality detecting function 173, the urgency judging function 174, the assessment information generating function 175, and the layout generating function 176 realized by the first processing circuitry 17 will be explained later, while following a procedure of performing a process (hereinafter "assessment information providing process") to provide the operator such as a radiologist with the assessment information.

The client apparatus 20 includes the second communication interface 21, the second memory 23, the second processing circuitry 25, the display 27, and the input interface 29. The client apparatus 20 may be used as another terminal device such as the image management terminal device. For example, the client apparatus 20 may be used by radiologists for creating image interpretation reports of medical images.

The second communication interface 21 is configured to perform data communication between the electronic medical record server apparatus 3, the RIS server 5, the PACS server 9, and the first communication interface 13. The communication standard used by the second communication interface 21 may be any standard. Examples thereof include Hearth Level 7 (HL7), DICOM, and a combination of the two. The second communication interface 21 is configured to output data obtained through the data communication with the various types of server apparatuses, to the second memory 23. The second communication interface 21 is configured to transmit the electrical signal of the input operation input to the input interface 29, to the first communication interface 13.

The second memory 23 is a storage device storing therein various types of information, such as an HDD, an SSD, or an integrated circuit storage device. Other than an HDD or an SDD, the second memory 23 may be a portable storage medium such as a CD, a DVD, or a flash memory or may be a driving device configured to read and write various types of information from and to a semiconductor memory element such as a RAM. The second memory 23 has stored therein various types of diagnosis/treatment information acquired from the various types of server apparatuses via the second communication interface 21. For example, the second memory 23 has stored therein the examination orders obtained by the second processing circuitry 25 via the second communication interface 21 and at least one medical image taken according to each of the examination orders. The second memory 23 has stored therein an examination list (which may be called a worklist) presenting a list of the plurality of examination orders obtained. The examination list will be explained later, while following the procedure of performing the assessment information providing process. The second memory 23 has stored therein a program related to a display function 251.

For example, the second processing circuitry 25 includes, as hardware resources, a processor such as a CPU, an MPU, or a GPU and a memory such as a ROM or a RAM. Further, the second processing circuitry 25 may be realized by using an ASIC, an FPGA, a CPLD, or an SPLD. The second processing circuitry 25 includes the display function 251 or the like. The display function 251 is stored in the second memory 23 in the form of a computer-executable program. By employing a processor configured to execute the program loaded into a memory, the second processing circuitry 25 is configured to execute the display function 251. In other words, the second processing circuitry 25 corresponds to a processor configured to realize the function corresponding to the program by reading and executing the program from the second memory 23.

That is to say, the second processing circuitry 25 that has read the program has the function corresponding to the read program. In this situation, the display function 251 does not necessarily have to be realized by a single piece of processing circuitry. It is also acceptable to structure processing circuitry by combining together a plurality of independent processors, so that the display function 251 is realized as a result of the processors executing the program. The second processing circuitry 25 realizing the display function 251 is an example of a display controlling unit. By employing the display function 251, the second processing circuitry 25 is configured to control the display 27 regarding various types of displays presented by the display 27. Details of the display function 251 will be explained later, while following the procedure of performing the assessment information providing process.

The display 27 is configured to display various types of information. For example, the display 27 is configured to output a Graphical User Interface (GUI) or the like used for receiving various types of operations from the operator. As the display 27, for example, it is possible to use a Liquid Crystal Display (LCD) device, a Cathode Ray Tube (CRT) display, an Organic Electroluminescence Display (OELD) device, a plasma display, or any other arbitrary display, as appropriate. Further, the display 27 may be of a desktop type or may be configured by using a tablet terminal or the like capable of wirelessly communicating with the medical information processing server apparatus 11.

When the urgency judging function 174 determines that the urgency is present, the display 27 is configured to display, in the examination list presenting the list of examination orders, the assessment information related to assessing the detected abnormality and urgency information indicating the urgency, so as to be positioned adjacent to any of the examination orders related to the abnormality. In that situation, the examination list may have an urgency cancellation region related to cancelling the display of the assessment information and the urgency information. While a thumbnail image of a medical image including an abnormality is displayed as the assessment information, the display 27 is configured to display an enlarged image obtained by enlarging the thumbnail image, as being triggered by a cursor being moved to the inside of the display region of the thumbnail image, under control of the display function 251. The display 27 is configured to cancel the display of the assessment information and the urgency information in response to a cancellation operation performed in the urgency cancellation region via the input interface 29. In response to a prescribed operation performed in the display region of the assessment information, the display 27 is configured to display, in the assessment layout, at least one medical image related to the abnormality.

The input interface 29 is configured to receive various types of input operations from the operator, to convert the received input operations into electrical signals, and to output the electrical signals to the second processing circuitry 25. Further, via the second communication interface 21 and the first communication interface 13, the converted electrical signals are output to the first processing circuitry 17. For example, the input interface 29 is configured to receive selecting instructions and various types of conditions from the operator. As the input interface 29, it is possible to use, for example, a mouse, a keyboard, a trackball, a switch, a button, a joystick, a touchpad, a touch panel display device, and/or the like, as appropriate.

In the present embodiment, the input interface 29 does not necessarily have to include one or more physical operation component parts such as the mouse, the keyboard, the trackball, the switch, the button, the joystick, the touchpad, the touch panel display device, and/or the like. For instance, possible examples of the input interface 29 include electrical signal processing circuitry configured to receive an electrical signal corresponding to an input operation from an external input device provided separately from the apparatus and to output the electrical signal to the first processing circuitry 17 and the second processing circuitry 25. Alternatively, the input interface 29 may be configured by using a tablet terminal or the like capable of wirelessly communicating with the medical information processing server apparatus 11.

Figure 2:
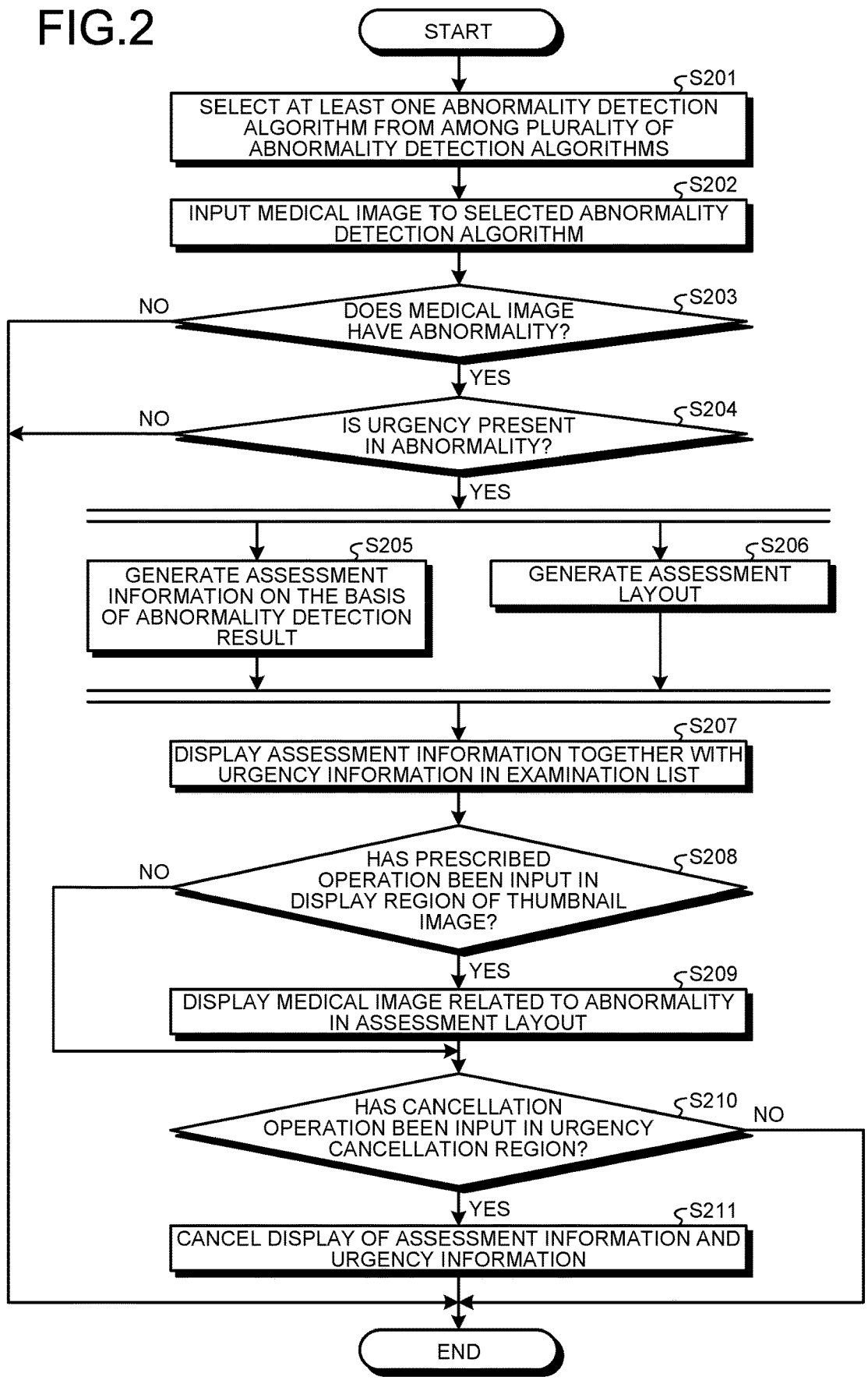
FIG. 2 is a flowchart illustrating an example of a procedure in an assessment information providing process according to the embodiment.

An overall configuration of the medical information processing system 1 has thus been explained. Next, a procedure in the assessment information providing process will be explained. FIG. 2 is a flowchart illustrating an example of the procedure in the assessment information providing process.

The assessment information providing process

Step S201:

By performing an existing image processing process, the selecting function 172 identifies an examined site, by identifying an anatomical landmark from the medical image. The selecting function 172 identifies whether or not contrast enhancement is present in the medical image, by analyzing the medical image while using an existing segmentation algorithm. From the appended information of the medical image, the selecting function 172 extracts information indicating whether or not contrast enhancement is present and the examination type such as the type of modality related to generating the medical image. By using the examination type, the examined site, whether or not contrast enhancement is present, and the type of modality, the selecting function 172 selects at least one abnormality detection algorithm to which the medical image is to be input, from among a plurality of abnormality detection algorithms. Alternatively, the selecting function 172 may select the abnormality detection algorithm, by extracting the examination purpose, the examination type, the examined site, whether or not contrast enhancement is present, and/or the like, from the examination order obtained either from the electronic medical record server apparatus 3 or from the RIS server 5.

For example, when the medical image is an image involving contrast enhancement while the examined site is the brain, the selecting function 172 selects an abnormality detection algorithm (hereinafter, "Large Vessel Occlusion [LVO] algorithm") related to cerebral infarction. As another example, when the medical image is a non-contrast-enhanced image while the examined site is the brain, the selecting function 172 selects an abnormality detection algorithm (hereinafter, "Intracranial Hemorrhage [ICH] algorithm") related to cerebral hemorrhage. As yet another example, when the medical image is a non-contrast-enhanced image while the examined site is the lungs, the selecting function 172 selects an abnormality detection algorithm (hereinafter, "oncology (tumors) algorithm") for detecting pulmonary nodules.

Step S202:

The abnormality detecting function 173 inputs the medical image to the selected abnormality detection algorithm. The abnormality detecting function 173 detects an abnormality from the input medical image by using the abnormality detection algorithm and outputs an abnormality detection result. The abnormality detection result is output in a JavaScript (registered trademark) Object Notation (JSON) format, for example. When no abnormality is detected from the medical image, the abnormality detecting function 173 outputs information (hereinafter, "abnormality undetected information") indicating that no abnormality was detected from the medical image.

Step S203:

When the abnormality detection result has been output by the abnormality detecting function 173 (step S203: Yes), the process at step S204 is performed. On the contrary, when no abnormality detection result has been output by the abnormality detecting function 173, i.e., when the abnormality detecting function 173 has output the abnormality undetected information (step S203: No), the assessment information providing process ends.

Step S204:

By using one of the abnormality relevance information and the type of the abnormality detection algorithm, the urgency judging function 174 judges whether or not urgency is present in the abnormality detected by the abnormality detecting function 173. More specifically, the urgency judging function 174 judges whether or not the urgency is present by extracting the disorder name from the abnormality relevance information and matching the extracted disorder name with the disorder urgency correspondence table. Examples of disorder names determined to have urgency include cerebral apoplexy, cerebral hemorrhage, and a large vessel occlusion. In contrast, examples of disorder names determined to have no urgency include a pulmonary nodule and various types of cancer. By matching the type of the abnormality detection algorithm used for detecting the abnormality with the algorithm urgency correspondence table, the urgency judging function 174 judges whether or not the urgency is present. Examples of abnormality detection algorithms with which it is determined that urgency is present include ICH and LVO algorithms. Examples of abnormality detection algorithms with which it is determined that no urgency is present include the oncology algorithm.

Alternatively, the urgency judging function 174 may judge whether or not the urgency is present by extracting the examination purpose from the examination order for the patient and matching the extracted examination purpose with the purpose-added correspondence table. FIG. 3 is a drawing illustrating an example of a purpose-added correspondence table ALT. As illustrated in FIG. 3, for example, when the examination purpose is a follow-up (to observe the progress) for the patient, the urgency judging function 174 determines that no urgency is present even when an abnormality is detected.

When the urgency judging function 174 determines that the urgency is present (step S204: Yes), the process at step S205 and the process at step S206 are performed. In this situation, the urgency judging function 174 transmits information indicating that the detected abnormality has urgency, to the client apparatus 20 via the first communication interface 13 and the second communication interface 21. On the contrary, when the urgency judging function 174 determines that no urgency is present (step S204: No), the assessment information providing process ends.

Step S205:

The assessment information generating function 175 generates assessment information on the basis of the abnormality detection result. For example, the assessment information includes at least one of: a thumbnail image of the medical image including the detected abnormality (i.e., the overlay image); the disorder name related to the detected abnormality; the name of the abnormality detection algorithm (hereinafter, "algorithm name"); and the correct output percentage related to the disorder name. In other words, the assessment information corresponds to information indicating a summary related to the abnormality detection result.

More specifically, the assessment information generating function 175 obtains, from the first memory 15, the correct output percentage corresponding to the abnormality detection result, by conducting a search in the first memory 15 while using the examined site in the medical image from which the abnormality was detected, the disorder name, and the algorithm name. The assessment information generating function 175 generates the thumbnail image by performing a prescribed shrinking process on the overlay image. In this situation, the assessment information generating function 175 brings the generated thumbnail image into association with the overlay image from which the thumbnail image was generated. Further, the assessment information generating function 175 extracts the disorder name, the algorithm name, and the correct output percentage from the abnormality relevance information in the abnormality detection result. The assessment information generating function 175 generates the assessment information by putting together the thumbnail image, the disorder name, the algorithm name, and the correct output percentage. The assessment information is transmitted to the client apparatus 20 via the first communication interface 13 and the second communication interface 21 and is stored into the second memory 23.

Step S206:

The layout generating function 176 generates an assessment layout on the basis of the overlay image. The assessment layout corresponds to a display layout suitable for an image interpretation of the medical image (hereinafter "key image") having the detected abnormality. When the key image is a CT image or an MRI image, the slice position of the key image corresponds to the slice position in which the abnormality was detected. On the basis of a plurality of medical images related to the patient, the layout generating function 176 generates at least one image suitable for diagnosing a disorder related to the abnormality, i.e., the image interpretation. For example, by performing a multi planar reconstruction on volume data related to the patient, the layout generating function 176 generates a three orthogonal cross-section image including the key image, an oblique image including the abnormality, a curved multi planar reconstruction (MPR) image including the abnormality, and/or the like.

Further, by performing a rendering process on the volume data, the layout generating function 176 may generate various types of rendering images (three-dimensional [3D] images) including the abnormality. In the following sections, to simplify the explanation, the medical image generated by the layout generating function 176 and including the abnormality will be referred to as an assessment reference image. Alternatively, the assessment reference image may be generated by the assessment information generating function 175. The assessment reference image corresponds to an image useful for assessment and diagnosing process on the abnormality detection result. The layout generating function 176 generates the assessment layout capable of displaying the key image and the assessment reference image. In this situation, the assessment layout may also be capable of further displaying the abnormality relevance information. The assessment layout, the key image, and the assessment reference image are transmitted to the client apparatus 20 via the first communication interface 13 and the second communication interface 21 and are stored into the second memory 23. Alternatively, the assessment layout, the key image, and the assessment reference information may be stored in the first memory 15. The layout generating function 176 appends link information between the thumbnail image and the assessment layout to the thumbnail image. Alternatively, the layout generating function 176 may append the link information to the assessment information. In the following sections, to simplify the explanation, it is assumed that the link information is appended to the thumbnail image.

Figure 4:
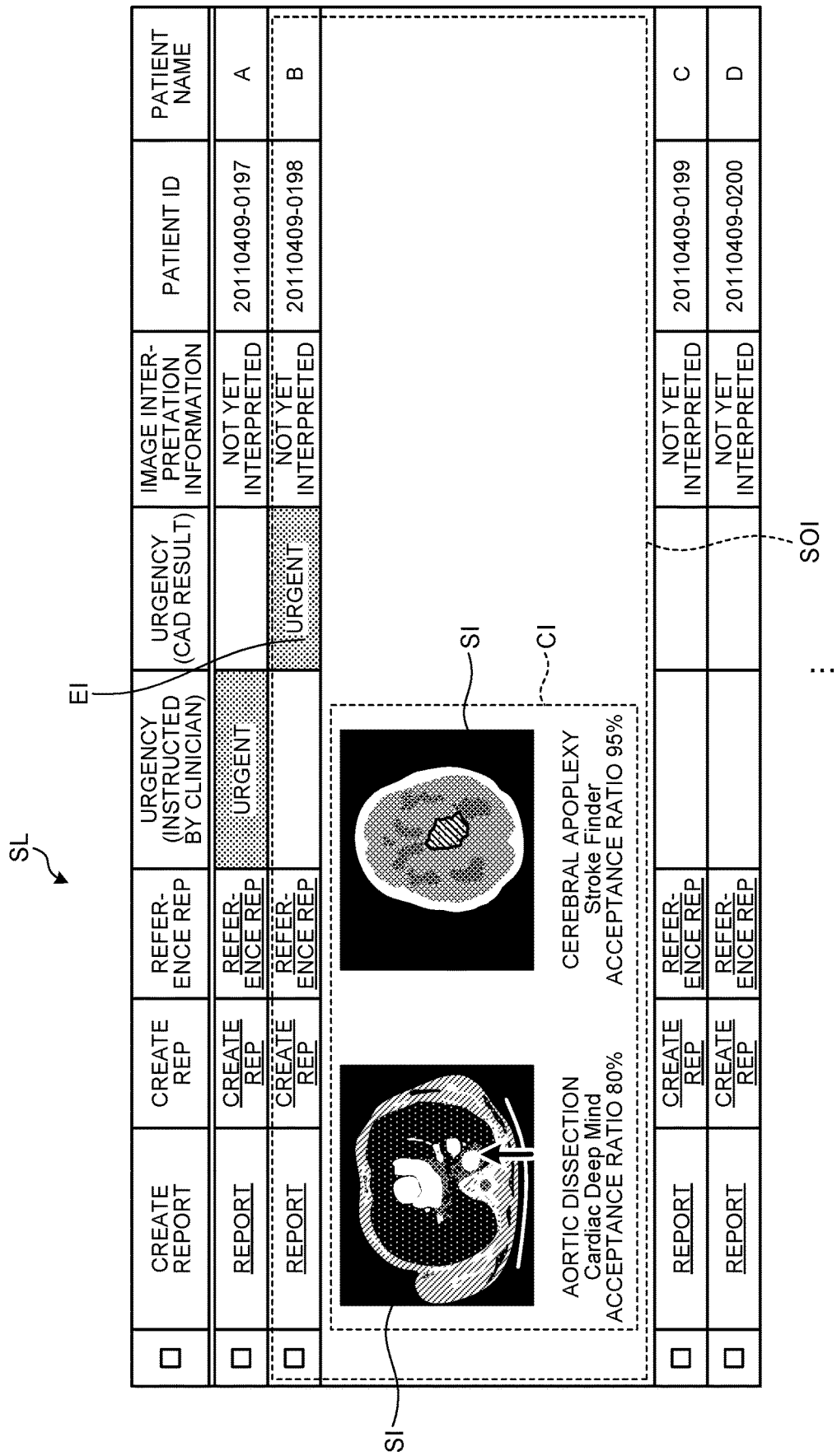
FIG. 4 is a drawing according to the embodiment illustrating examples of assessment information and urgency information in an examination list.

Step S207:

In the examination list, the display function 251 causes the display 27 to display the assessment information and the urgency information indicating the urgency so as to be positioned adjacent to any of the examination orders related to the abnormality. FIG. 4 is a drawing illustrating examples of assessment information CI and urgency information EI indicating urgency in an examination list SL. In the examination list SL, for example, examination orders are arranged either according to the sequential order in which the examination orders were received or according to the sequential order in which the medical images were acquired. With the examination order positioned in the uppermost line of the examination list SL, an "urgent" flag is displayed according to an instruction from the clinician for patient A. In addition, when no urgency is indicated under the item of the judgment result by the urgency judging function 174 (hereinafter, "CAD result"), the urgency information EI is in a non-display state. In the examination list SL in FIG. 4, although the two columns, namely one from a clinician and the other from the CAD result, are indicated as columns related to urgency, possible embodiments are not limited to this example. For instance, a flag for an urgent image interpretation instructed by a clinician and a flag for an urgent image interpretation based on a CAD result may be displayed in a single column in the examination list SL while using mutually-different display modes.

As illustrated in FIG. 4, for the examination order SOI in the second line of the examination list SL, because no urgency instruction was issued by the clinician for patient B, no "emergency" flag is displayed. However, for the examination order SOI in the second line, because it has been determined that urgency is present in the analysis result on the medical image made by the abnormality detection algorithm, a character string "urgent" is displayed as urgency information EI under the item of the CAD result. In addition, with the examination order SOI in the second line, the assessment information CI is displayed.

In the assessment information CI in FIG. 4, the disorder name "aortic dissection", the name "Cardiac Deep Mind" of the abnormality detection algorithm that output the disorder name, and the correct output percentage (ACCEPTANCE RATIO) "80%" of the abnormality detection algorithm that output the disorder name are displayed together with a thumbnail image SI of the key image. Further, in the assessment information CI, the disorder name "cerebral apoplexy", the name "Stroke Finder" of the abnormality detection algorithm that output the disorder name, and the correct output percentage (ACCEPTANCE RATIO) "95%" of the abnormality detection algorithm that output the disorder name are displayed together with another thumbnail image SI of the key image.

Figure 5:
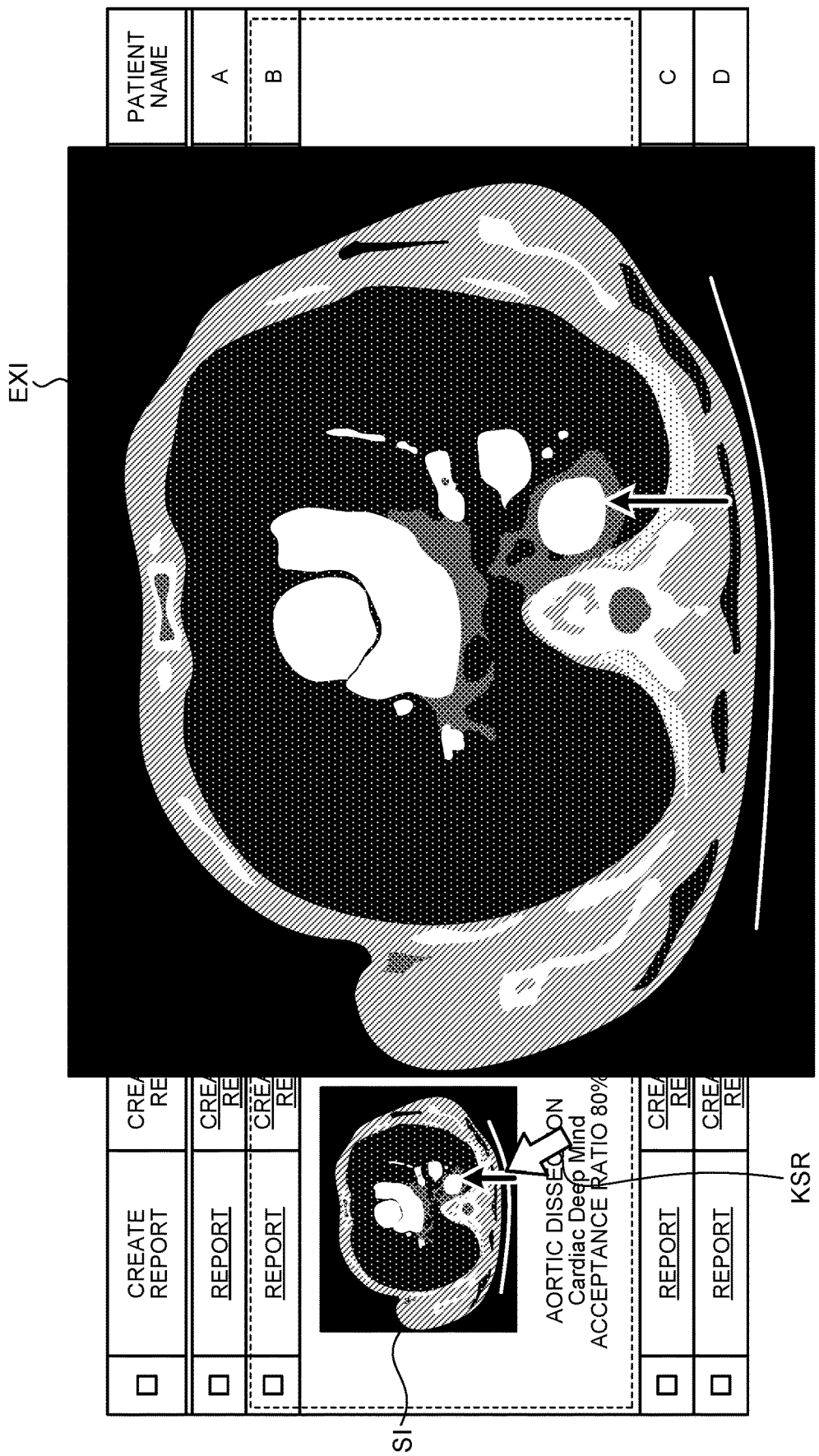
FIG. 5 is a drawing according to the embodiment illustrating an example of displaying an enlarged image when a cursor has been moved to the inside of a display region of a thumbnail image corresponding to an "aortic dissection" in the assessment information.

When a cursor displayed on the display 27 is moved to the inside of the display region of any of the thumbnail images SI according to an instruction from the operator such as a radiologist, the display function 251 causes the display 27 to display an enlarged image obtained by enlarging the thumbnail image SI so as to be superimposed on the examination list SL. Alternatively, in place of the enlarged image, the display function 251 may cause the display 27 to display the key image in a display region larger than that of the thumbnail image SI. FIG. 5 is a drawing illustrating an example of displaying an enlarged image EXI when a cursor KSR has been moved to the inside of the display region of the thumbnail image SI corresponding to the "aortic dissection" in the assessment information CI. When the position of the cursor KSR has moved out of the display region of the thumbnail image SI, the display function 251 cancels the display of the enlarged image EXI.

Figure 6:
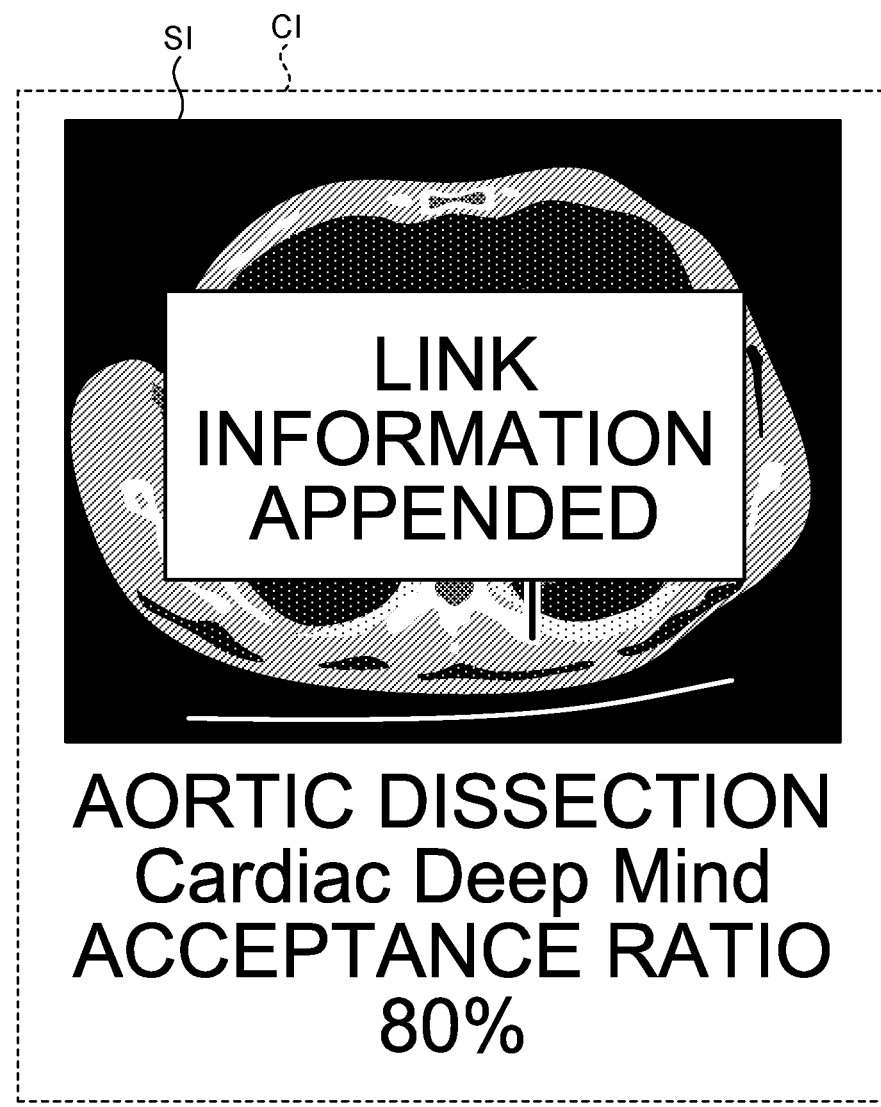
FIG. 6 is a drawing according to the embodiment illustrating an example of a thumbnail image to which link information is appended, in the assessment information related to the "aortic dissection" illustrated in FIG. 4.

Step S208:

When a prescribed operation is input in the display region of any of the thumbnail images SI (step S208: Yes), the process at step S209 is performed. The prescribed operation is one simple operation (e.g., a single click operation using the mouse) performed while the cursor KSR is in the state of having been moved in the display region of the thumbnail image SI. When the prescribed operation is not input in the display region of the thumbnail image SI (step S208: No), the process at step S210 is performed. In this situation, when the link information is appended to the assessment information CI, the region where the prescribed operation is valid is the display region of the assessment information CI. FIG. 6 is a drawing illustrating an example of the thumbnail image SI to which the link information is appended in the assessment information CI related to the "aortic dissection" illustrated in FIG. 4. Although the thumbnail image SI in FIG. 6 has the writing "LINK INFORMATION APPENDED", the text "LINK INFORMATION APPENDED" is not displayed in the display presented by the display 27.

Figure 7:
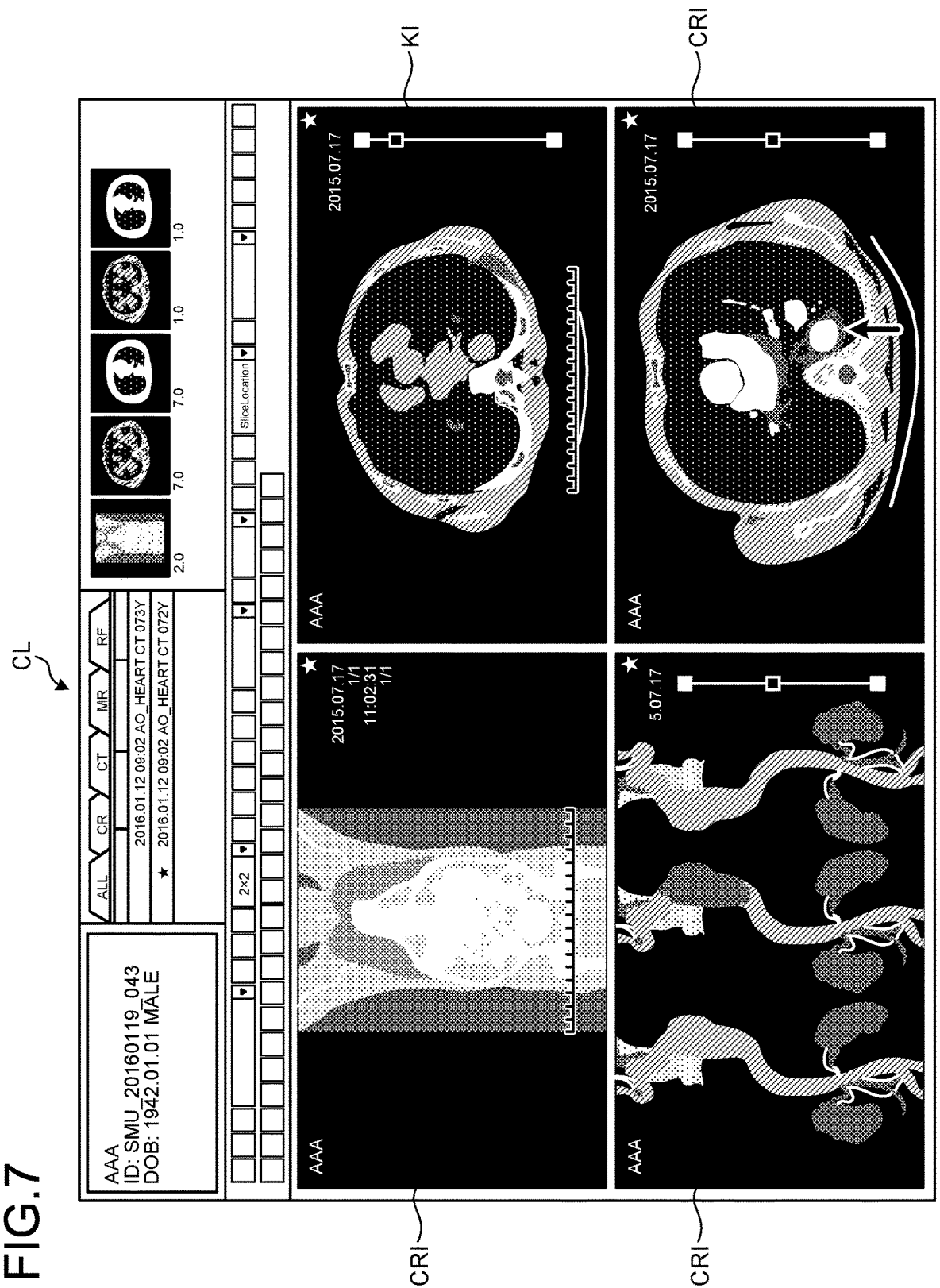
FIG. 7 is a drawing according to the embodiment illustrating examples of a key image and an assessment reference image displayed in an assessment layout.

Step S209:

In response to the prescribed operation performed in the display region of the assessment information CI, the display function 251 displays, in the assessment layout, at least one medical image related to the detected abnormality, i.e., the assessment reference image. When a single click operation is input while the cursor KSR is in the state of having been moved in the display region of any of the thumbnail images SI illustrated in FIG. 4 or 6, the display function 251 causes the display 27 to display, in the assessment layout, the key image and the assessment reference image. FIG. 7 is a drawing illustrating examples of a key image KI and an assessment reference image CRI displayed in an assessment layout CL. As illustrated in FIG. 7, in the assessment layout CL, the operator such as a radiologist is provided with an image interpretation environment to interpret the key image KI and the assessment reference image CRI.

Step S210:

When the assessment information CI is displayed while being positioned adjacent to any of the examination orders, the examination list SL has the urgency cancellation region related to cancelling the display of the assessment information CI and the urgency information EI (hereinafter, "cancelling the urgency display"). The urgency cancellation region may be, as illustrated in FIG. 4 for example, a blank region in the examination order SOI or the region where the urgency information EI is displayed. Possible embodiments of the urgency cancellation region are not limited to the above examples. It is possible to set the urgency cancellation region in an arbitrary position on the display screen of the examination list SL. Via the input interface 29, when the operator inputs an instruction to cancel the urgency display (step S210: Yes), the process at step S211 is performed. The input of the instruction to cancel the urgency display corresponds, for example, to a single click operation using the mouse performed while the cursor KSR is in the state of having been moved in the urgency cancellation region. When no instruction to cancel the urgency display is input (step S210: No), the assessment information providing process ends.

Step S211:

In response to the input of the instruction to cancel the urgency display, the display function 251 cancels the display of the assessment information CI and the urgency information EI in the examination list SL. In other words, in response to the operation to cancel the urgency display performed within the urgency cancellation region, the display 27 cancels the display of the assessment information CI and the urgency information EI. As a result, in the examination list SL, the assessment information CI and the urgency information EI are in a non-display state. Thus, the assessment information providing process ends. The processes at steps S201 through S211 are performed, for example, every time a medical image acquired by the medical image diagnosis apparatus 7 according to an examination order is transmitted to either the medical information processing server apparatus 11 or an analysis apparatus.

In the medical information processing system 1 according to the embodiment described above, at least one abnormality detection algorithm to which the medical image is to be input is selected on the basis of the medical image related to the patient, and the abnormality is detected from the medical image by inputting the medical image to the abnormality detection algorithm, so as to judge whether or not urgency is present in the disorder related to the abnormality, on the basis of one of the abnormality relevance information and the type of the abnormality detection algorithm. When it is determined that the urgency is present, the assessment information CI and the urgency information EI are displayed so as to be positioned adjacent to any of the examination orders related to the abnormality in the examination list SL. In other words, in the medical information processing system 1 in the present example, when the abnormality detection result output by the abnormality detection algorithm has urgency, the assessment information CI including at least one of the thumbnail image SI, the disorder name related to the abnormality, the name of the abnormality detection algorithm, and the correct output percentage, together with the urgency information EI, is displayed in the examination list SL.

In other words, in the examination list SL, it is possible to provide the operator such as a radiologist with the information that makes it possible to judge correctness of the abnormality detection result. With this arrangement, by using the medical information processing system 1, the operator is able to assess, within the examination list SL, whether or not the image needs to be urgently interpreted and the correctness of the abnormality detection result, regarding the medical image from which the abnormality was detected by the abnormality detection algorithm, without the need for full-scale image interpretation preparation by causing a medical image interpretation screen to be displayed from the examination list SL.

Further, in the medical information processing system 1, it is judged whether or not urgency is present, by further using the examination purpose in the examination order for the patient related to the medical image. Accordingly, when the examination purpose is a post-surgery follow-up or a post-diagnosis/treatment follow-up, the disorder related to the abnormality detected by the abnormality detection algorithm is determined to have no urgency. It is therefore possible to reduce the workload of the operator related to urgent image interpretations.

Further, in the medical information processing system 1, in the situation where the display 27 is displaying the thumbnail image SI of the medical image including the abnormality detected by the abnormality detection algorithm as the assessment information CI, the display 27 is configured to display the enlarged image EXI obtained by enlarging the thumbnail image SI, as being triggered by the cursor KSR being moved to the inside of the display region of the thumbnail image SI. With this arrangement, the enlarged image EXI is displayed as a result of moving the cursor KSR to the inside of the display region of the thumbnail image SI, without the need to perform an additional operation such as a click operation on the mouse. It is therefore possible to reduce the workload in the operations of the operator.

Further, in the medical information processing system 1, the examination list SL has the urgency cancellation region related to cancelling the display of the assessment information CI and the urgency information EI so that, in response to the cancelling operation performed within the urgency cancellation region, the display of the assessment information CI and the urgency information EI in the examination list SL is cancelled. With this arrangement, it is possible to cancel the display of the assessment information CI and the urgency information EI, by performing the single operation while the cursor KSR is in the state of having been moved in the urgency cancellation region. It is possible to reduce the workload in the operations of the operator.

Further, in the medical information processing system 1, when it is determined that the urgency is present in relation to the detected abnormality, the assessment layout CL is generated in which it is possible to assess the abnormality and which is related to displaying the medical image including the abnormality. In response to the prescribed operation performed in the display region of the assessment information CI, at least one medical image related to the abnormality is displayed in the assessment layout CL. In other words, in the medical information processing system 1, because the assessment layout capable of displaying the key image and the assessment reference image is generated in advance, it is possible to immediately provide the operator with an image interpretation environment where the disorder in question can be diagnosed and assessed, with one simple operation such as a single click operation performed in the display region of the thumbnail image SI, without the need to search for the medical image having the abnormality prior to the image interpretation. With these arrangements, it is possible to improve efficiency in the assessment and the diagnosing process on the abnormality detection result having urgency for an image interpretation.

Further, in a modification example of the present embodiment, the medical information processing system 1 may be incorporated in a Hospital Information System (HIS). Further, the medical information processing system 1 may be realized with cloud computing or the like. In that situation, the first communication interface 13, the first memory 15, and the first processing circuitry 17 are installed in a server provided in a network.

Modification Examples

In a modification example, assessment information includes at least one of: an index (hereinafter, "reliability index") related to reliability of the abnormality detected by the abnormality detection algorithm; and an index (hereinafter, "priority index") related to priority of treatment on the abnormality. The reliability index includes a reliability value or a confidence level indicating reliability or credibility of the abnormality detection result (an analysis result) output from the abnormality detection algorithm; an average value of a plurality of reliability values related to similar medical cases and/or medical images from the past; the most frequent value among the reliability values; the median of the reliability values; a histogram of the reliability values; the standard deviation of the reliability values; a confidence interval related to the reliability values; and/or the like.

The reliability values and the confidence level are each a numerical value indicating a degree of likelihood of accuracy with respect to the abnormality detected by the abnormality detection algorithm (confidence of the abnormality detection algorithm), for example. The average value of the reliability values, the most frequent value among the reliability values, the median of the reliability values, the histogram of the reliability values, the standard deviation of the reliability values, the confidence interval related to the reliability values, and the like can each serve as an index when the operator judges the reliability of the abnormality detected by the abnormality detection algorithm. Further, the histogram of the reliability values, the standard deviation of the reliability values, and the confidence interval related to the reliability values each correspond to data indicating variability of the plurality of reliability values of a plurality of similar abnormalities detected in the past.

For example, the priority index may be numerical value data of a value (e.g., a mismatch ratio) indicating the prospect for a recovery of the patient with treatment on the abnormality; a degree to which the prognosis of the abnormality becomes good with treatment; a degree indicating validity of the treatment; a priority ranking of the treatment on the abnormality; and/or the like. For example, the priority index can serve as a basis for judging whether or not an image interpretation or treatment should be performed with priority on the detected abnormality.

By using the abnormality detection algorithm, the abnormality detecting function 173 is configured to output one or both of the reliability index and the priority index, together with the abnormality detection result. In this situation, the abnormality detecting function 173 may output the one or both of the reliability index and the priority index, by inputting the abnormality detection result to another algorithm different from the abnormality detection algorithm. The different algorithm may be, for example, a trained model such as a DNN or a rule-based analysis program. Alternatively, one or both of the reliability index and the priority index may be generated by the assessment information generating function 174, on the basis of the abnormality detection result output from the abnormality detection algorithm.

Further, one of the abnormality detecting function 173 and the assessment information generating function 174 may be configured to calculate and update the average value of the reliability values, the most frequent value of the reliability values, the median of the reliability values, the histogram of the reliability values, the standard deviation of the reliability values, the confidence interval related to the reliability values, and/or the like in the reliability index, on the basis of the reliability index corresponding to the abnormality detection result output by the abnormality detecting function 173 and a reliability index related to similar medical cases and medical images from the past stored in the first memory 15. In this situation, the average value, the most frequent value, the median, the histogram, the standard deviation, the confidence interval, and/or the like having been updated are stored into the first memory 15.

The first memory 15 is configured to store therein the average value of the plurality of reliability values related to the similar medical cases and medical images regarding the abnormality detection result, the most frequent value of the reliability values, the histogram of the reliability values, the standard deviation of the reliability values, and the confidence interval related to the reliability values. Further, the average value, the most frequent value, the histogram, the standard deviation, and the confidence interval may be updated as appropriate every time a new reliability index is output by the abnormality detecting function 173.

Another assessment information generating process

The processing procedure in the present modification example is similar to that in the flowchart in FIG. 6. In the following sections, the steps in the different processes will be explained.

Step S205:

The assessment information generating function 175 generates assessment information by putting together the thumbnail image, the disorder name, the algorithm name, the correct output percentage, and the reliability index. In another example, the assessment information generating function 175 generates assessment information by putting together the thumbnail image, the disorder name, the algorithm name, the correct output percentage, and the priority index. Alternatively, the assessment information generating function 175 may generate assessment information by putting together the thumbnail image, the disorder name, the algorithm name, the correct output percentage, the reliability index, and the priority index.

Figure 8:
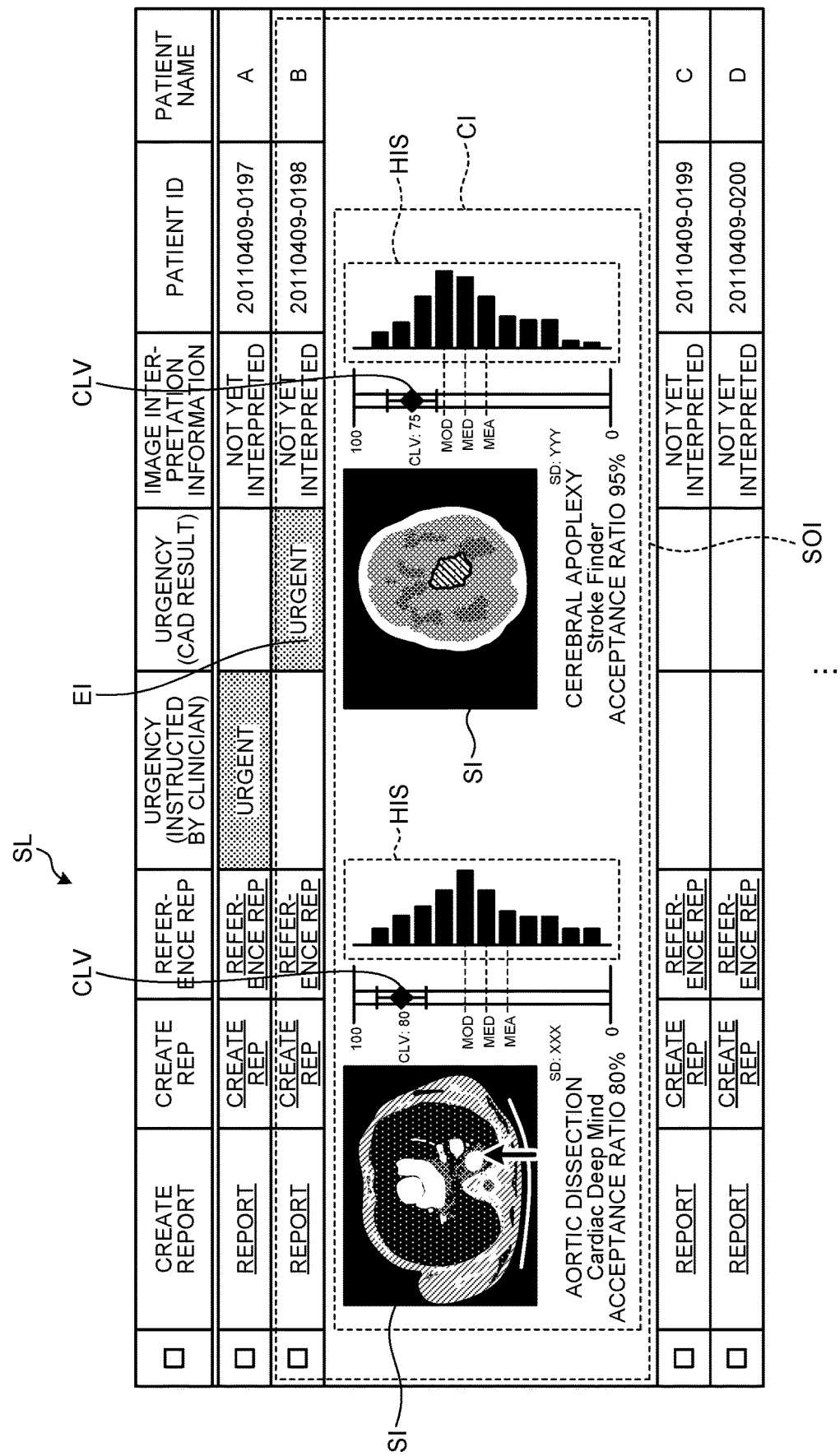
FIG. 8 is a drawing illustrating examples of assessment information and urgency information in an examination list according to a modification example of the embodiment.

Step S207:

In the examination list, the display function 251 causes the display 27 to display the assessment information and the urgency information indicating the urgency, so as to be positioned adjacent to any of the examination orders related to the abnormality. FIG. 8 is a drawing illustrating examples of the assessment information CI and the urgency information EI indicating the urgency in the examination list SL. The difference between FIG. 8 and FIG. 4 is that, in the assessment information CI, reliability indices are displayed in accordance with the abnormality detection results. As illustrated in FIG. 8, the reliability CLV is indicated in the range from 0 to 100, for example. As illustrated in FIG. 8, for example, the reliability CLV of the abnormality detection result from "Cardiac Deep Mind" is 80. As another example, as illustrated in FIG. 8, the reliability CLV of the abnormality detection result from "Stroke Finder" is 75. The reliability values being displayed as illustrated in FIG. 8 may each be displayed with a bar (an error bar) indicating a confidence interval. Further, as illustrated in FIG. 8, a histogram HIS indicating a distribution of frequency of a plurality of reliability values may be displayed in the vicinity of the bar indicating the range of placements of reliability values. In that situation, the histogram HIS may display the most frequent value MOD of the reliability values, the median MED of the reliability values, and an average value MEA of the reliability values.

Figure 9:
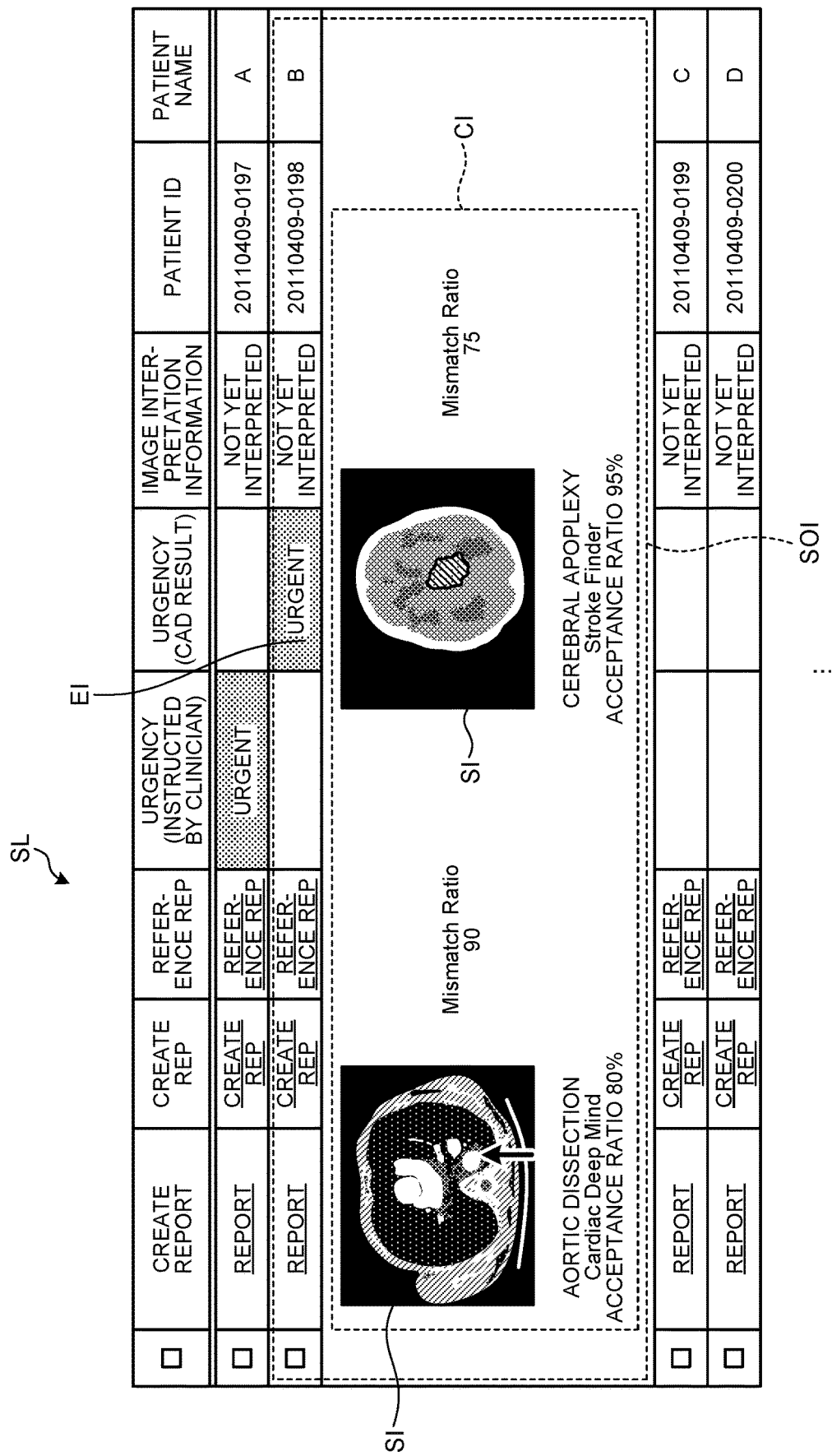
FIG. 9 is a drawing illustrating the examples of the assessment information and the urgency information in the examination list according to another modification example of the embodiment.

FIG. 9 is a drawing illustrating examples of the assessment information CI and urgency information EI indicating the urgency in the examination list SL. The difference between FIG. 9 and FIG. 4 is that, in the assessment information CI, priority indices are displayed in accordance with the abnormality detection results. In FIG. 9, mismatch ratios are displayed as the priority indices. For example, as illustrated in FIG. 9, the mismatch ratio of the abnormality detection result from "Cardiac Deep Mind" is 90, whereas the mismatch ratio of the abnormality detection result from "Stroke Finder" is 75. In an application example of the present modification example, when the assessment information includes the reliability indices and the priority indices, the display 27 is configured to further display the priority indices such as the mismatch ratios in the assessment information CI illustrated in FIG. 8.

In the medical information processing system 1 according to the modification example of the embodiment described above, the assessment information further includes one or both of: the reliability index related to the reliability of the detected abnormality; and the priority index related to the priority of the treatment on the abnormality. Accordingly, the display 27 is configured to further display one or both of the reliability index and the priority index. With this arrangement, according to the present modification example, it is possible to present the operator with the reliability of the abnormality detection results from the abnormality detection algorithm and the statistical information related to the reliability. In addition, according to the present modification example, it is possible to present the operator with the information related to the priority of the treatment on the detected abnormality. Consequently, by using the medical information processing system 1 according to the present modification example, it is possible to easily assess whether or not the image needs to be urgently interpreted and the correctness of the abnormality detection result. It is therefore possible to reduce the workload of the operator in determining the sequential order of image interpretations regarding urgent image interpretations. Because the other advantageous effects are the same as those of the above embodiment, explanations thereof will be omitted.

When a technical concept of the present embodiment is realized as a medical information processing method, the medical information processing method includes: judging, on a basis of one of a type of at least one abnormality detection algorithm to which a medical image related to an examined subject is to be input and information relevant to an abnormality detected by inputting the medical image to the abnormality detection algorithm, whether or not urgency is present in a disorder related to the abnormality, causing the display 27 to display, in the examination list SL presenting the list of examination orders, the assessment information CI related to assessing the abnormality and the urgency information EI indicating the urgency, so as to be positioned adjacent to any of the examination orders related to the abnormality. Because the processing procedure and advantageous effects of the medical information processing method are the same as those of the above embodiment, explanations thereof will be omitted.

When a technical concept of the present embodiment is realized as a medical information processing program, the medical information processing program is configured to cause a computer to realize: judging, on a basis of one of a type of at least one abnormality detection algorithm to which a medical image related to an examined subject is to be input and information relevant to an abnormality detected by inputting the medical image to the abnormality detection algorithm, whether or not urgency is present in a disorder related to the abnormality, causing the display 27 to display, in the examination list SL presenting the list of examination orders, the assessment information CI related to assessing the abnormality and the urgency information EI indicating the urgency, so as to be positioned adjacent to any of the examination orders related to the abnormality.

For example, it is also possible to realize the assessment information providing process by installing the medical information processing program in computers of the PACS server 9 and an integration server in a hospital information system and loading these programs into a memory. In that situation, the programs capable of causing the computers to implement the method may be distributed as being stored in a storage medium such as a magnetic disc (e.g., a hard disk), an optical disc (e.g., a CD-ROM or a DVD), or a semiconductor memory. Because the processing procedure and advantageous effects of the medical information processing program are the same as those of the above embodiment, explanations thereof will be omitted.

According to at least one aspect of the embodiments described above, it is possible to provide the information related to assessing the correctness of the abnormality detected from the medical image. Accordingly, by using the medical information processing system 1 of the present disclosure, it is possible to reduce the workload of the operation in relation to assessing the correctness of the abnormality detection result having urgency for an image interpretation and the like, and it is also possible to decrease time and labor. It is therefore possible to improve throughput of the image interpretations.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing system, comprising: processing circuitry configured to
select an abnormality detection algorithm to which a medical image related to an examined subject is to be input,
detect information relevant to an abnormality by inputting the medical image to the selected abnormality detection algorithm,
determine whether or not urgency is present in a disorder related to the abnormality based on the detected information,
cause a display, when it is determined that the urgency is present, to display, in an examination list presenting a list of examination orders, assessment information related to assessing the abnormality, and urgency information indicating the urgency, so as to be positioned adjacent to any of the examination orders related to the abnormality, wherein the displayed assessment information includes a percentage of correct outputs related to a disorder; an index related to a reliability of the detected abnormality; and an index related to a priority of treatment on the abnormality, wherein the processing circuitry is further configured to select the abnormality detection algorithm to which the medical image is to be input, by analyzing the medical image related to the examined subject, and the displayed assessment information includes a thumbnail image of the medical image including the abnormality, and the display displays an enlarged image obtained by enlarging the thumbnail image, in response to a cursor being moved to an inside of a display region of the thumbnail image.

2. The medical information processing system according to claim 1, wherein the processing circuitry is further configured to determine whether or not the urgency is present, by further using an examination purpose in the examination order for the examined subject related to the medical image.

3. The medical information processing system according to claim 1, wherein the examination list has an urgency cancellation region related to cancelling the display of the assessment information and the urgency information, and in response to an operation for the cancellation performed in the urgency cancellation region, the display cancels the display of the assessment information and the urgency information.

4. The medical information processing system according to claim 1, wherein when it is determined that the urgency is present, the processing circuitry is further configured to generate an assessment layout in which it is possible to assess the abnormality and which is related to displaying the medical image including the abnormality, and in response to a prescribed operation performed in a display region of the assessment information, the display displays, in the assessment layout, at least one medical image related to the abnormality.

5. The medical information processing system according to claim 1, wherein the processing circuitry is further configured to detect the abnormality from the medical image, by inputting the medical image to the selected abnormality detection algorithm.

6. The medical information processing system of claim 1, wherein the processing circuitry is further configured to cause the display to stop displaying the urgency information in response to a user selecting the displayed urgency information.

7. A medical information processing method, comprising:

determining, based on an abnormality detection algorithm to which a medical image related to an examined subject is to be input and information relevant to an abnormality detected by inputting the medical image to the abnormality detection algorithm, whether or not urgency is present in a disorder related to the abnormality; and causing, when it is determined that the urgency is present, a display to display, in an examination list presenting a list of examination orders, assessment information related to assessing the abnormality, and urgency information indicating the urgency, so as to be positioned adjacent to any of the examination orders related to the abnormality, wherein the displayed assessment information includes a percentage of correct outputs related to a disorder; an index related to a reliability of the detected abnormality; and an index related to a priority of treatment on the abnormality, wherein the method further includes selecting the abnormality detection algorithm to which the medical image is to be input, by analyzing the medical image related to the examined subject, and the displayed assessment information includes a thumbnail image of the medical image including the abnormality, and the display displays an enlarged image obtained by enlarging the thumbnail image, in response to a cursor being moved to an inside of a display region of the thumbnail image.

* * * * *